United States Patent
Palmer

(10) Patent No.: US 10,123,886 B2
(45) Date of Patent: Nov. 13, 2018

(54) CLEARANCE ENHANCER FOR LOWER LIMB PROSTHESIS

(71) Applicant: Jeffrey Ray Palmer, Swisher, IA (US)

(72) Inventor: Jeffrey Ray Palmer, Swisher, IA (US)

( * ) Notice: Subject to any disclaimer, the term of this patent is extended or adjusted under 35 U.S.C. 154(b) by 0 days.

(21) Appl. No.: 15/392,310

(22) Filed: Dec. 28, 2016

(65) Prior Publication Data

US 2018/0177613 A1 Jun. 28, 2018

(51) Int. Cl.
*A61F 2/66* (2006.01)
*A61F 2/60* (2006.01)
*A61F 2/50* (2006.01)
*A61F 2/76* (2006.01)

(52) U.S. Cl.
CPC .............. *A61F 2/66* (2013.01); *A61F 2/6607* (2013.01); *A61F 2/76* (2013.01); *A61F 2002/5021* (2013.01); *A61F 2002/5083* (2013.01); *A61F 2002/607* (2013.01); *A61F 2002/6642* (2013.01); *A61F 2002/6678* (2013.01)

(58) Field of Classification Search
CPC .. A61F 2/66; A61F 2/6607; A61F 2/76; A61F 2002/6614; A61F 2002/6621; A61F 2002/6628; A61F 2002/6635; A61F 2002/6642; A61F 2002/665; A61F 2002/6657; A61F 2002/6664; A61F 2002/6678; A61F 2002/6671; A61F 2002/6685; A61F 2002/6692; A61F 3/00
See application file for complete search history.

(56) References Cited

U.S. PATENT DOCUMENTS

| 5,376,141 | A | * | 12/1994 | Phillips | ..................... A61F 2/66 623/38 |
| 2007/0100465 | A1 | * | 5/2007 | Egan | ..................... A61F 2/5044 623/52 |
| 2007/0106397 | A1 | * | 5/2007 | Townsend | ................ A61H 3/02 623/52 |

(Continued)

OTHER PUBLICATIONS

Cyriac, Biju Babu. Meet Shalini Saraswathi-The Quadruple Amputee Who's Running the World 10K Marathon in Bengaluru. Times of India. May 12, 2016.*

(Continued)

*Primary Examiner* — Thomas J Sweet
*Assistant Examiner* — Christine Bahena
(74) *Attorney, Agent, or Firm* — Lane & Waterman LLP

(57) ABSTRACT

A lower limb prosthesis for a person is provided that comprises a foot prosthesis having a heel plate for contacting the ground and an ankle plate extending vertically from the heel plate when the heel plate is in ground contact, a leg prosthesis having an upper end portion mountable to the body of the person and a lower end portion, and a clearance enhancer. The clearance enhancer is in the form of a generally L-shaped plate, the plate including a base plate and an upper plate extending generally perpendicularly from the base plate. The base plate is configured to be connected to the lower end of the leg prosthesis. The upper plate includes a number of mounting openings to receive a corresponding number of fasteners for connecting the upper plate to the ankle plate of the foot prosthesis so that the lower portion of the leg prosthesis overlaps the ankle plate of the foot prosthesis.

8 Claims, 4 Drawing Sheets

(56) References Cited

U.S. PATENT DOCUMENTS

| | | | | |
|---|---|---|---|---|
| 2008/0281436 A1* | 11/2008 | Townsend | ............... | A61F 2/60 |
| | | | | 623/52 |
| 2009/0157197 A1* | 6/2009 | Bonacini | ............... | A61F 2/66 |
| | | | | 623/55 |
| 2011/0213471 A1* | 9/2011 | Jonsson | ............... | A61F 2/66 |
| | | | | 623/53 |
| 2013/0085581 A1* | 4/2013 | Lecomte | ............... | A61F 2/66 |
| | | | | 623/55 |
| 2014/0005801 A1* | 1/2014 | Van der Watt | ............ | A61F 2/76 |
| | | | | 623/53 |
| 2014/0243998 A1* | 8/2014 | Phillips | ............... | A61F 2/66 |
| | | | | 623/55 |
| 2016/0206446 A1* | 7/2016 | Smith | ............... | A61F 2/66 |

OTHER PUBLICATIONS

Sabolich, Scott. Building a Track-Serviceable Running Prosthesis. O&P Edge Magazine. Mar. 2009.*
Ottobock3. Ottobock Website 4R206 TF Sport Adapter-Instructions for Use. pp. 1-4 and 12-19. Published Mar. 11, 2013.*
Ottobock. Ottobock Website. Running Prostheses Systems. Verified by the Wayback Machine Nov. 23, 2015.*

* cited by examiner

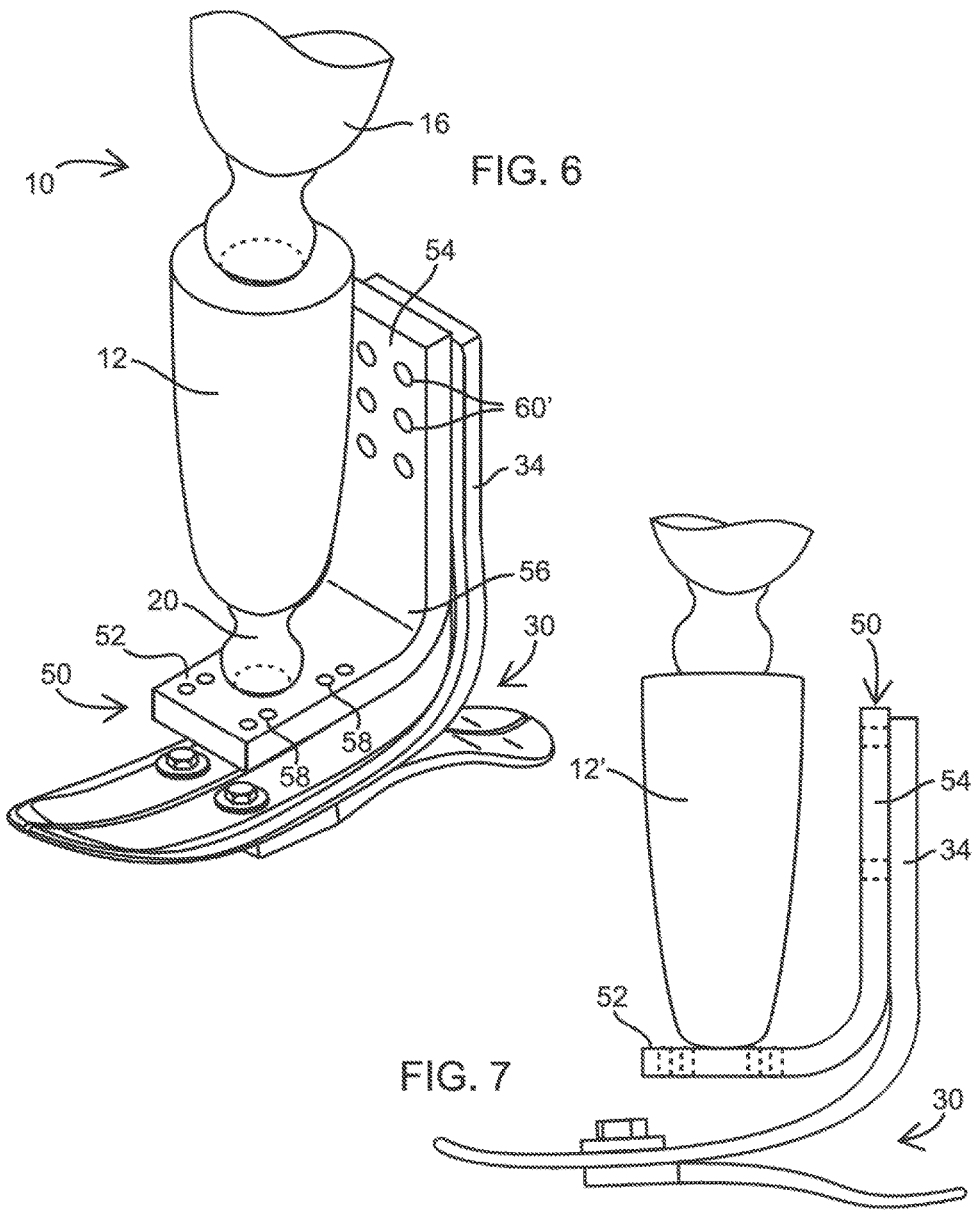

CLEARANCE ENHANCER FOR LOWER LIMB PROSTHESIS

BACKGROUND

The present disclosure relates to prostheses for the lower limb of a person and particularly to an improvement for the engagement of a prosthetic foot to a lower limb prosthesis.

One form of lower limb prosthesis 10 is shown in FIG. 1 which includes a lower leg or transfemoral pylon 12, connected at its upper end to a prosthetic knee joint 14 and at its lower end to a prosthetic foot 18. The knee joint is connected to a socket 16 adapted for a secure fit to the intact proximal limb. It is understood that the pylon 12 may be part of a total limb prosthesis system. The lower leg pylon 12 is connected to the prosthetic foot 18 by a prosthetic ankle joint 20 as is known in the art.

The foot prosthesis 18 shown in FIG. 1 represents a "low energy" prosthesis in the sense that the foot prosthesis is generally rigid. The prosthesis 18 does not have the ability to flex or the ability to absorb and return energy in flexion in the manner of a physiologically normal foot. Consequently, more active lower leg amputees may desire a "high energy" foot prosthesis, such as the prosthesis 30 shown in FIG. 2. The prosthesis 30 includes a foot plate 32 that is curved upward to an ankle plate 34. The ankle plate 34 includes mounting elements 36 for attaching the foot prosthesis 30 to an ankle joint or a lower leg pylon in a known manner. The foot prosthesis 30 further includes a heel plate 38 fastened to the foot plate 32 in a known manner. The foot plate and the heel plate are curved and configured to flex in the manner of a leaf spring. The foot plate 32 and heel plate 38 thus absorb energy as the person applies his/her weight to the foot prosthesis, thereby flexing or bending the plates. This energy is returned as the plates act as a leaf spring to return to their original unflexed state.

Such "high energy" foot prostheses are desirable for active persons, such as athletes and children. Foot prostheses of the type shown in FIG. 2 are readily adapted for amputees of normal or taller stature due to the overall dimensions of the prosthetic foot necessary to provide sufficient functionality. However, these necessary dimensions of the prosthetic foot make "high energy" prostheses problematic for persons of smaller stature or amputees with longer residual limbs such as long transfemoral amputees, long transtibial amputees, and Symes amputees, that are limited to a low "build height" for the lower limb prostheses. These amputees are often limited to choosing a prosthetic knee capable of high activity levels or a prosthetic foot capable of high activity levels, but not both.

There is a need for a lower limb prosthesis system that allows the smaller stature amputee and the longer residual limb amputee to enjoy the benefits of high energy, high activity prostheses. There is also a need for a prosthesis system that allows the person to readily swap foot prostheses between "low energy" and "high energy" prosthesis as the occasion dictates.

SUMMARY OF THE DISCLOSURE

A clearance enhancer is provided for a lower limb prostheses system, and particularly for engagement between a transfemoral prosthesis and a "high energy" foot prosthesis. In one aspect of the disclosure, a lower limb prosthesis for a person is provided that comprises a foot prosthesis having a heel plate for contacting the ground and an ankle plate extending vertically from the heel plate when the heel plate is in ground contact, a leg prosthesis having an upper end portion mountable to the body of the person and a lower end portion, and a clearance enhancer. The clearance enhancer is in the form of a generally L-shaped plate, the plate including a base plate and an upper plate extending generally perpendicularly from the base plate. The base plate is configured to be connected to the lower end of the leg prosthesis. The upper plate includes a number of mounting openings to receive a corresponding number of fasteners for connecting the upper plate to the ankle plate of the foot prosthesis. In one feature of the disclosure, the number of mounting openings are arranged so that the lower end portion of the leg prosthesis overlaps the ankle plate of the foot prosthesis when the clearance enhancer is connected to the foot prosthesis.

BRIEF DESCRIPTION OF THE DRAWINGS

FIG. 6 is a perspective view of the clearance enhancer shown in FIGS. 3-5 connected between a transfemoral prosthesis, with a prosthetic ankle joint, and a foot prosthesis, according to one feature of the present disclosure.

FIG. 7 is a side view of the clearance enhancer shown in FIGS. 3-5 connected between an alternative transfemoral prosthesis and a foot prosthesis, according to a further feature of the present disclosure.

DETAILED DESCRIPTION

Figure 1:
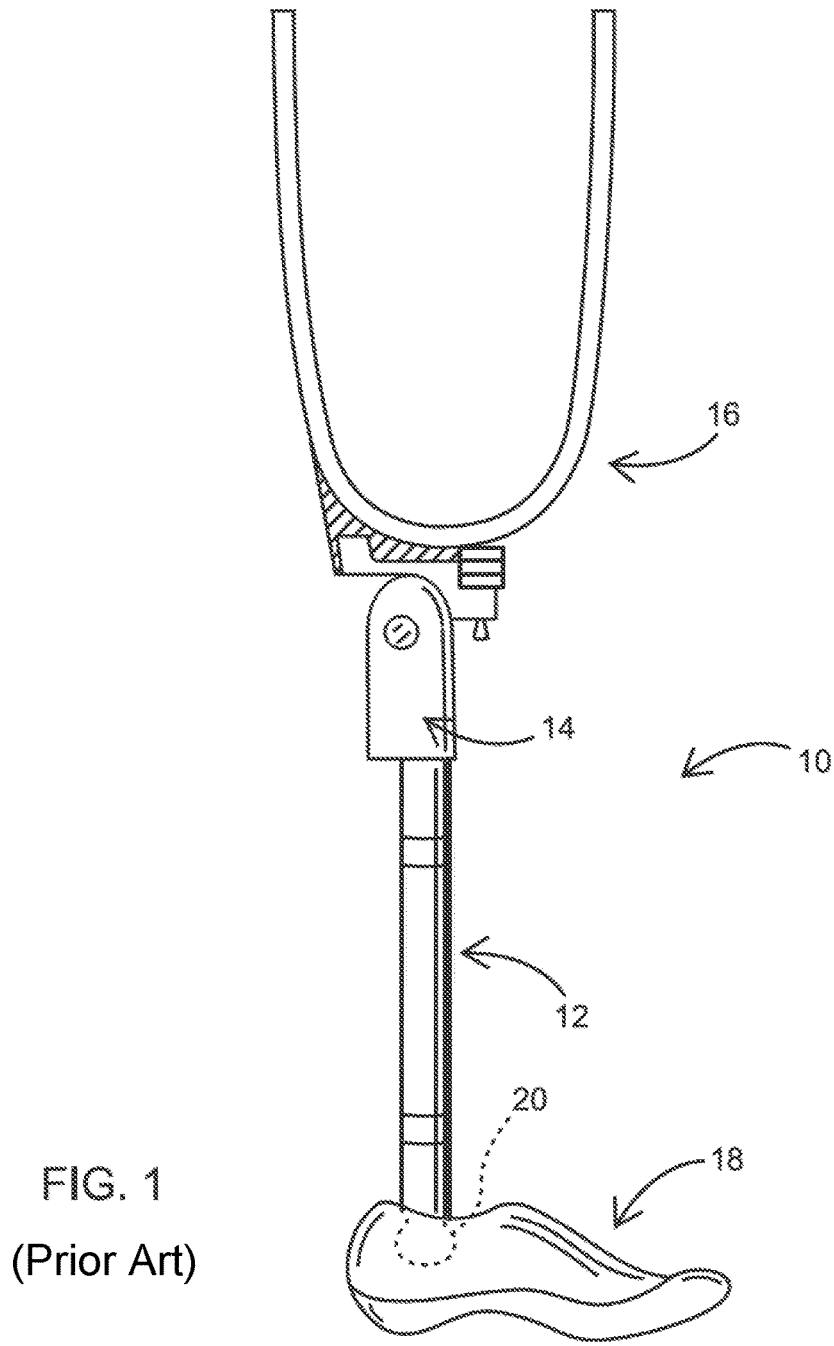
FIG. 1 is a side view of a lower leg prosthesis.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Figure 4:
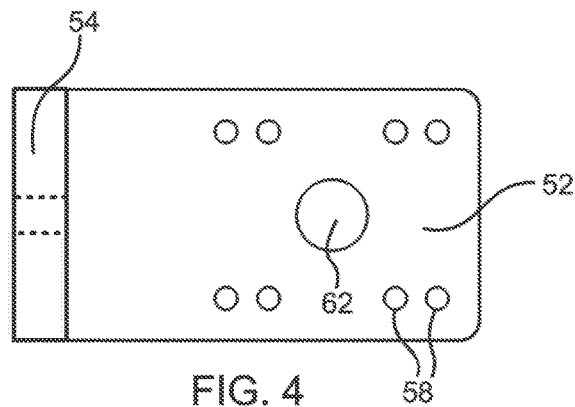
FIG. 4 is a top view of the clearance enhancer shown in FIG. 3.
Figure 3:
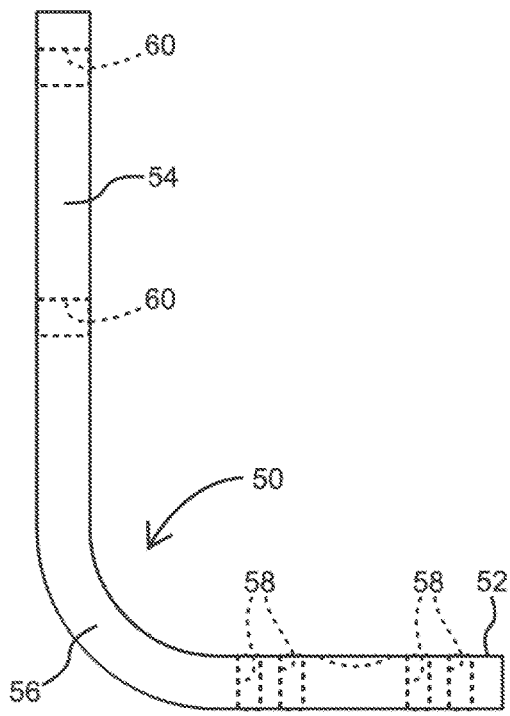
FIG. 3 is a side view of a clearance enhancer according to one aspect of the present disclosure.

A clearance enhancer 50 according to the present disclosure is shown in FIGS. 3-4. The clearance enhancer 50 is a generally L-shaped body having a base plate 52, a curved portion 56 and an upper plate 54. The base plate 52 includes a number of mounting openings 58 adapted to receive fasteners for attaching the base plate 52 to the lower end of a transfemoral prosthesis. The base plate 52 may further define a depression 62 in the surface of the base plate that is adapted to receive an articulating component of a prosthetic ankle joint. The mounting openings 58 may be arranged to align with corresponding attachment openings in the transfemoral prosthesis.

Figure 2:
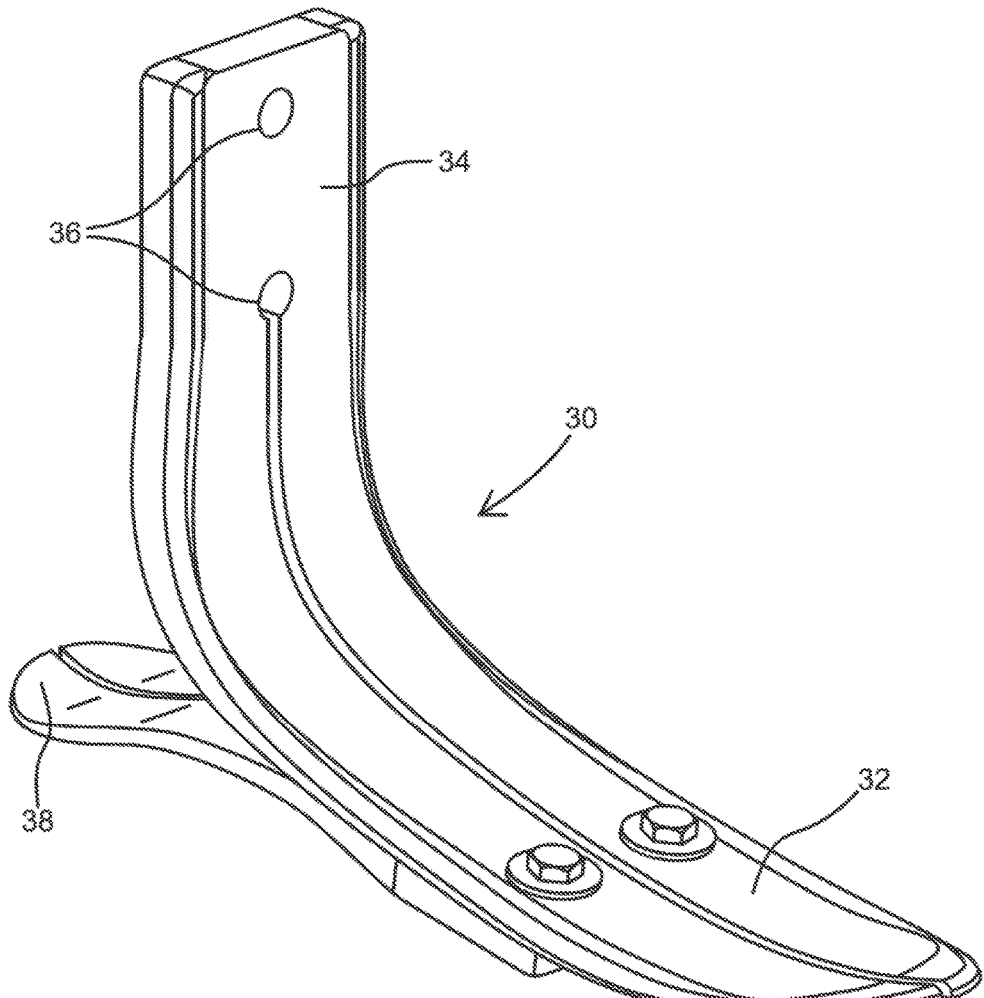
FIG. 2 is a perspective view of a "high energy" foot prosthesis.
Figure 5:
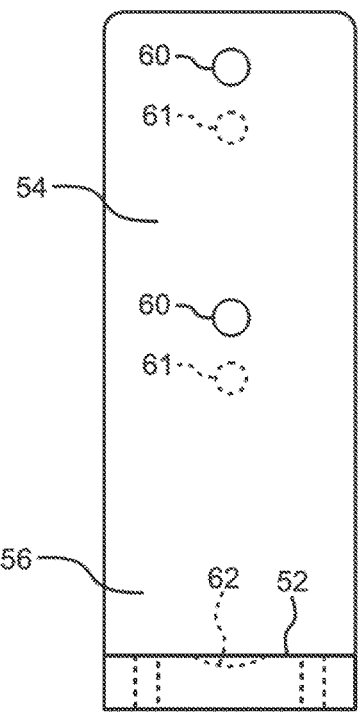
FIG. 5 is an end view of the clearance enhancer shown in FIG. 3.

The curved portion 56 is bent so that the upper plate 54 is at a predetermined angle relative to the base plate 52. In the illustrated embodiment, the two plates are generally perpendicular to each other, although other angular relationships are contemplated as may be appropriate for the physiology of the person wearing the prosthesis. The upper plate 54 includes a plurality of mounting openings 60 adapted to receive fasteners for attaching the upper plate 54 to the ankle plate of a foot prosthesis. In the illustrated embodiment, two mounting openings 60 are provided to correspond to the two attachment openings 36 in the foot prosthesis 30 shown in FIG. 2. However, it is contemplated that the upper plate 54 may include additional mounting openings 61, as shown in FIG. 5, or an array of mounting openings 60', as shown in FIG. 6, to accommodate the attachment opening configuration of the foot prosthesis. It is further contemplated that the array of openings can permit adjustment of the position of the upper plate 54 in relation to the ankle plate 34 of the foot prosthesis.

The clearance enhancer 50 may be formed from a single plate bent to the L-shape shown in FIG. 3. In one embodiment, the plate may be 0.375" thick 6061 Aluminum. The material and plate thickness may be selected to be generally rigid so that the clearance enhancer 50 does not flex appreciably under active load. The plate may be formed of other suitably strong materials, such as carbon fiber, titanium and certain plastics. The selected material must be sufficiently strong so that the clearance enhancer can be appropriately rigid without excessive thickness of the plate. The enhancer 50 may have a width of 1.750" and a length from the back surface of the upper plate to the end of the base plate 52 of about 3.250", which is sufficient for engagement to most conventional transfemoral prostheses. The enhancer 50 may have a height from the underside of the base plate to the top of the upper plate 54 of 4.875", which is sufficient for engagement to most conventional foot prostheses, particularly the "high energy" or "high activity" foot prostheses.

The clearance enhancer 50 is depicted in FIG. 6 mounted to one form of transfemoral prosthesis 10 and one form of foot prosthesis 30. The transfemoral prosthesis includes an articulating ankle joint component 20 that engages the depression 62 in the base plate 52 of the clearance enhancer. Other mounting elements may be provided for fastening the clearance enhancer to the lower end of the lower leg pylon 12 of the prosthesis 10. The clearance enhancer 50 may incorporate a bearing element for contact with the articulating ankle joint component 20. The upper plate 54 of the clearance enhancer 50 is fastened to the ankle portion 34 of the foot prosthesis 30 using conventional fasteners. As shown in FIG. 6, the upper plate includes an array of mounting openings 60' that allows some adjustment of the position of the clearance enhancer on the foot prosthesis.

FIG. 7 shows the clearance enhancer 50 mounted to an alternative transfemoral prosthesis that does not include an articulating ankle joint component. In this embodiment, the base plate 52 is fastened directly to the lower end of the lower leg pylon 12' using convention fasteners. The upper plate 54 of the clearance enhancer may be fastened to the ankle portion 34 of the foot prosthesis as described above.

For a taller stature person, the ankle portion 34 of the foot prosthesis would be attached directly to the transfemoral prosthesis 10. This attachment configuration is too high for the smaller stature person. It can be appreciated that the clearance enhancer 50 of the present disclosure allows a person of smaller stature to use the "high energy" or "active" foot prosthesis, such as the prosthesis 30. The clearance enhancer essentially lowers the mounting location for the transfemoral prosthesis 10 relative to the ankle portion 34 of the foot prosthesis so that the lower portion of the transfemoral prosthesis overlaps the ankle portion of the foot prosthesis. The amount of vertical overlap between the transfemoral prosthesis 10 and the foot prosthesis 30 may be adjustable, such as by way of the mounting opening arrays discussed above.

The array of mounting openings is thus arranged so that the clearance between the heel plate of the foot prosthesis and the lower end of the leg prosthesis is improved for a person of smaller stature. In particular, the clearance is reduced to allow the smaller stature person to use the conventionally sized foot prosthesis. In the specific embodiment of the L-shaped plate described above, the 4.875" height of the upper plate 54 allows the lower end portion of the leg prosthesis to overlap the ankle plate by about 4.5". The clearance between the lower end of the leg prosthesis and the heel plate of the foot prosthesis is thus reduced by about 4.5" from the clearance for a conventional leg prosthesis-foot prosthesis interface. With an array of mounting openings, the amount of overlap can be adjusted by appropriate selection of the mounting openings used to connect the clearance enhancer to the ankle plate of the foot prosthesis.

It is further contemplated that the clearance enhancer may be removed so that the transfemoral prosthesis can be fastened to a different foot prosthesis, or the clearance enhancer itself maybe mounted to other foot prostheses by way of the mounting openings 60, 61, 60'.

It is contemplated that the clearance enhancer 50 may be provided in various sizes appropriate to the height of the amputee wearing the prosthesis. The clearance enhancer may also be provided with different relative angles between the base plate 52 and the upper plate 54 to match the physiology of the person.

The present disclosure should be considered as illustrative and not restrictive in character. It is understood that only certain embodiments have been presented and that all changes, modifications and further applications that come within the spirit of the disclosure are desired to be protected.

What is claimed is:
1. A lower limb prosthesis for a person comprising:
a foot prosthesis having a heel plate for contacting the ground and an ankle plate extending vertically from the heel plate when the heel plate is in substantially horizontal ground contact, said ankle plate including a number of mounting elements;
a leg prosthesis having an upper end portion mountable to the body of the person and a lower end portion; and
a clearance enhancer including a generally L-shaped plate, the plate including a base plate and an upper plate extending generally perpendicularly from the base plate, the base plate configured to be connected to the lower end of the leg prosthesis and the upper plate including a number of mounting openings to receive a corresponding number of fasteners for connecting the upper plate to the ankle plate of the foot prosthesis, the number of mounting openings arranged so that the lower end portion of the leg prosthesis overlaps the ankle plate of the foot prosthesis when at least some of the number of mounting openings are aligned with at least some of the number of mounting elements of the ankle plate such that the clearance enhancer is connected to the foot prosthesis with said base plate positioned vertically between said number of mounting openings of said upper plate and said heel plate of said foot prosthesis.

2. The lower limb prosthesis of claim 1, wherein said generally L-shaped plate of said clearance enhancer is formed from aluminum.

3. The lower limb prosthesis of claim 1, wherein said generally L-shaped plate of said clearance enhancer has a thickness of 0.375 inches.

4. The lower limb prosthesis of claim 1, wherein said generally L-shaped plate has a height from the underside of the base plate to the top of the upper plate of 4.875 inches.

5. The lower limb prosthesis of claim 1, wherein said generally L-shaped plate has a width of 1.750 inches.

6. The lower limb prosthesis of claim 1, wherein said generally L-shaped plate has a length from the back surface of the upper plate to the end of the base plate of 3.250 inches.

7. The lower limb prosthesis of claim 1, wherein said number of mounting openings are provided in number and location to correspond to mounting elements on the ankle plate of the foot prosthesis.

8. The lower limb prosthesis of claim 1, wherein:
   the leg prosthesis includes an articulating joint component at the lower end portion; and
   the base plate of the clearance enhancer includes a dimple configured to receive the articulating joint component.

\* \* \* \* \*